US009782582B2

(12) United States Patent
Govea et al.

(10) Patent No.: US 9,782,582 B2
(45) Date of Patent: Oct. 10, 2017

(54) SYSTEMS AND METHODS FOR MAKING AND USING ELECTRICAL STIMULATION SYSTEMS TO REDUCE RF-INDUCED TISSUE HEATING

(71) Applicant: Boston Scientific Neuromodulation Corporation, Valencia, CA (US)

(72) Inventors: Michael X. Govea, Glendale, CA (US); Joshua Dale Howard, Winnetka, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/077,459

(22) Filed: Mar. 22, 2016

(65) Prior Publication Data

US 2016/0279409 A1 Sep. 29, 2016

Related U.S. Application Data

(60) Provisional application No. 62/139,545, filed on Mar. 27, 2015.

(51) Int. Cl.
*A61N 1/08* (2006.01)
*A61N 1/375* (2006.01)
*A61N 1/05* (2006.01)

(52) U.S. Cl.
CPC ............. *A61N 1/08* (2013.01); *A61N 1/05* (2013.01); *A61N 1/0551* (2013.01); *A61N 1/3752* (2013.01); *A61N 2001/086* (2013.01)

(58) Field of Classification Search
None
See application file for complete search history.

(56) References Cited

U.S. PATENT DOCUMENTS 5,131,388 A 7/1992 Pless et al.
5,336,246 A 8/1994 Dantanarayana
(Continued)

FOREIGN PATENT DOCUMENTS

WO 2010126943 11/2010

OTHER PUBLICATIONS

Rezai, A. R., et al., "Neurostimulation system used for deep brain stimulation (DBS): MR safety issues and implications of failing to follow guidelines." Investigative Radiology, 39:300-303: 2004.
(Continued)

*Primary Examiner* — Brian T Gedeon
(74) *Attorney, Agent, or Firm* — Lowe Graham Jones PLLC; Bruce E. Black

(57) ABSTRACT

An electrical stimulation lead includes a lead body having a distal end, a proximal end, and a longitudinal length; electrodes disposed along the distal end of the lead body; terminals disposed along the proximal end of the lead body; a non-conducting core extending along lead body; and conductors extending along the lead body to electrically couple the electrodes to the terminals. The conductors include a first conductor and a second conductor arranged along the core with a non-conducting gap between the first and the second conductors. Each of the first and the second conductors includes an inner conductor portion with a first electrical resistivity and an outer conductor portion having a second electrical resistivity that is at least twice the first electrical resistivity. The outer conductor portion is disposed exclusively radially outward from the inner conductor portion.

20 Claims, 9 Drawing Sheets

(56) References Cited

U.S. PATENT DOCUMENTS

| | | |
|---|---|---|
| 5,699,801 A | 12/1997 | Atalar et al. |
| 5,825,608 A | 10/1998 | Duva et al. |
| 5,928,145 A | 7/1999 | Ocali et al. |
| 6,031,375 A | 2/2000 | Atalar et al. |
| 6,181,969 B1 | 1/2001 | Gord |
| 6,240,317 B1 | 5/2001 | Villaseca et al. |
| 6,263,229 B1 | 7/2001 | Atalar et al. |
| 6,394,956 B1 | 5/2002 | Chandrasekaran et al. |
| 6,408,202 B1 | 6/2002 | Lima et al. |
| 6,508,765 B2 | 1/2003 | Suorsa et al. |
| 6,510,345 B1 | 1/2003 | Van Bentem |
| 6,516,227 B1 | 2/2003 | Meadows et al. |
| 6,549,800 B1 | 4/2003 | Atalar et al. |
| 6,606,513 B2 | 8/2003 | Lardo et al. |
| 6,609,029 B1 | 8/2003 | Mann et al. |
| 6,609,032 B1 | 8/2003 | Woods et al. |
| 6,628,980 B2 | 9/2003 | Atalar et al. |
| 6,673,999 B1 | 1/2004 | Wang et al. |
| 6,675,033 B1 | 1/2004 | Lardo et al. |
| 6,701,176 B1 | 3/2004 | Halperin et al. |
| 6,714,809 B2 | 3/2004 | Lee et al. |
| 6,741,892 B1 | 5/2004 | Meadows et al. |
| 6,824,515 B2 | 11/2004 | Suorsa et al. |
| 6,898,454 B2 | 5/2005 | Atalar et al. |
| 6,904,307 B2 | 6/2005 | Karmarkar et al. |
| 7,015,393 B2 | 3/2006 | Weiner et al. |
| 7,133,714 B2 | 11/2006 | Karmarkar et al. |
| 7,194,294 B2 | 3/2007 | Panescu et al. |
| 7,236,816 B2 | 6/2007 | Kumar et al. |
| 7,244,150 B1 | 7/2007 | Brase et al. |
| 7,412,276 B2 | 8/2008 | Halperin et al. |
| 7,437,193 B2 | 10/2008 | Parramon et al. |
| 7,551,953 B2 | 6/2009 | Lardo et al. |
| 7,561,906 B2 | 7/2009 | Atalar et al. |
| 7,599,729 B2 | 10/2009 | Atalar et al. |
| 7,620,453 B1 | 11/2009 | Propato et al. |
| 7,672,734 B2 | 3/2010 | Anderson et al. |
| 7,761,165 B1 | 7/2010 | He et al. |
| 7,778,682 B2 | 8/2010 | Kumar et al. |
| 7,822,460 B2 | 10/2010 | Halperin et al. |
| 7,822,484 B1 | 10/2010 | Zhao et al. |
| 7,844,319 B2 | 11/2010 | Susil et al. |
| 7,848,788 B2 | 12/2010 | Tulley et al. |
| 7,949,395 B2 | 5/2011 | Kuzma |
| 7,957,783 B2 | 6/2011 | Atalar et al. |
| 7,974,706 B2 | 7/2011 | Moffitt et al. |
| 8,055,351 B2 | 11/2011 | Atalar et al. |
| 8,108,028 B2 | 1/2012 | Karmarkar |
| 8,175,710 B2 | 5/2012 | He |
| 8,224,450 B2 | 7/2012 | Brase |
| 8,322,026 B2 | 12/2012 | McDonald |
| 8,335,570 B2 | 12/2012 | McDonald |
| 8,340,782 B2 | 12/2012 | McDonald et al. |
| 8,364,278 B2 | 1/2013 | Pianca et al. |
| 8,364,279 B2 | 1/2013 | McDonald et al. |
| 8,380,277 B2 | 2/2013 | Atalar et al. |
| 8,380,324 B2 | 2/2013 | McDonald et al. |
| 8,433,421 B2 | 4/2013 | Atalar et al. |
| 8,478,423 B2 | 7/2013 | McDonald et al. |
| 8,509,876 B2 | 8/2013 | Karmarkar |
| 8,649,842 B2 | 2/2014 | Atalar et al. |
| 8,688,226 B2 | 4/2014 | Atalar et al. |
| 8,788,058 B2 * | 7/2014 | Li ............................ A61N 1/05 607/115 |
| 2001/0014820 A1 | 8/2001 | Gielen et al. |
| 2004/0181177 A1 | 9/2004 | Lee et al. |
| 2005/0070972 A1 | 3/2005 | Wahlstrand et al. |
| 2005/0222633 A1 | 10/2005 | Edvardsson |
| 2007/0150036 A1 | 6/2007 | Anderson |
| 2008/0039898 A1 | 2/2008 | Lim et al. |
| 2008/0051854 A1 | 2/2008 | Bulkes et al. |
| 2008/0243218 A1 | 10/2008 | Bottomley et al. |
| 2008/0262584 A1 | 10/2008 | Bottomley et al. |
| 2009/0149906 A1 | 6/2009 | Ameri et al. |
| 2009/0234368 A1 | 9/2009 | Gore |
| 2009/0259272 A1 | 10/2009 | Reddy et al. |
| 2009/0270956 A1 | 10/2009 | Vase et al. |
| 2010/0057175 A1 | 3/2010 | McDonald et al. |
| 2011/0112612 A1 | 5/2011 | Rahman |
| 2011/0137414 A1 | 6/2011 | Litzke et al. |
| 2011/0144449 A1 | 6/2011 | Ortiz et al. |
| 2011/0152999 A1 | 6/2011 | Hastings et al. |
| 2011/0234155 A1 | 9/2011 | Chen et al. |
| 2011/0257703 A1 | 10/2011 | Kerber et al. |
| 2012/0016355 A1 | 1/2012 | George et al. |
| 2012/0035616 A1 | 2/2012 | Olsen et al. |
| 2012/0041528 A1 | 2/2012 | Mehdizadeh et al. |
| 2012/0041529 A1 | 2/2012 | Olsen et al. |
| 2012/0123500 A1 | 5/2012 | Erickson |
| 2012/0158072 A1 | 6/2012 | Venook et al. |
| 2012/0191167 A1 | 7/2012 | McDonald et al. |
| 2012/0221074 A1 | 8/2012 | Brase et al. |
| 2013/0105071 A1 | 5/2013 | DiGiore et al. |
| 2013/0304170 A1 | 11/2013 | Foster et al. |
| 2014/0034377 A1 | 2/2014 | Vij |
| 2014/0058482 A1 | 2/2014 | Gupta et al. |
| 2014/0135614 A1 | 5/2014 | Venook et al. |
| 2014/0214130 A1 | 7/2014 | Lopez et al. |
| 2014/0277316 A1 * | 9/2014 | Chen ...................... A61N 1/05 607/116 |
| 2015/0031975 A1 | 1/2015 | Atalar et al. |
| 2015/0073506 A1 | 3/2015 | Gupta et al. |
| 2015/0374977 A1 | 12/2015 | Howard et al. |

OTHER PUBLICATIONS

Nyenhuis, J. A., et al., "MRI and implanted medical devices: basic interactions with an emphasis on heating." IEEE Transactions on Device and Materials Reliability, 5:467-478; 2005.

International Search Report and Written Opinion for PCT/US2016/023589 dated Aug. 23, 2016.

* cited by examiner

SYSTEMS AND METHODS FOR MAKING AND USING ELECTRICAL STIMULATION SYSTEMS TO REDUCE RF-INDUCED TISSUE HEATING

CROSS-REFERENCE TO RELATED APPLICATIONS

This application claims the benefit under 35 U.S.C. §119 (e) of U.S. Provisional Patent Application Ser. No. 62/139,545, filed Mar. 27, 2015, which is incorporated herein by reference.

FIELD

The present invention is directed to the area of implantable electrical stimulation systems and methods of making and using the systems. The present invention is also directed to implantable electrical stimulation leads or lead extensions that include elements for reducing tissue heating or other deleterious effects due to radio frequency (RF) irradiation, as well as methods of making and using the leads, lead extensions, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead including a lead body having a distal end, a proximal end, and a longitudinal length; electrodes disposed along the distal end of the lead body; terminals disposed along the proximal end of the lead body; a non-conducting core extending along lead body; and conductors extending along the lead body to electrically couple the electrodes to the terminals. The conductors include a first conductor and a second conductor arranged along the core with a non-conducting gap between the first and the second conductors. Each of the first and the second conductors includes an inner conductor portion with a first electrical resistivity and an outer conductor portion having a second electrical resistivity that is at least twice the first electrical resistivity. The outer conductor portion is disposed exclusively radially outward from the inner conductor portion.

In at least some embodiments, a radial thickness of the outer conductor portion is at least equal to a skin depth of RF radiation at 64 MHz. In at least some embodiments, each of the plurality of conductors is wedge-shaped. In at least some embodiments, each of the conductors is separated from each adjacent one of the conductors by a wedge-shaped gap. In at least some embodiments, the second electrical resistivity is at least five times the first electrical resistivity. In at least some embodiments, the inner conductor portion is formed of MP35N alloy, platinum, or platinum/iridium alloy and the outer conductor portion is formed of gold or silver.

Another embodiment is an implantable electrical stimulation lead including a lead body having a distal end, a proximal end, and a longitudinal length; electrodes disposed along the distal end of the lead body; terminals disposed along the proximal end of the lead body; a non-conducting core extending along lead body; and conductors extending along the lead body to electrically couple the plurality of electrodes to the plurality of terminals. At least one of the conductors includes wide regions and narrow regions alternating with the wide regions, where each wide region has a maximum width and each narrow region has a minimum width. The maximum width of each wide region is at least three times the minimum width of each narrow region.

In at least some embodiments, the maximum width of each wide region is at least five times the minimum width of each narrow region. In at least some embodiments, the maximum width of each wide region is at least ten times the minimum width of each narrow region. In at least some embodiments, a plurality of the conductors each includes a plurality of wide regions and a plurality of narrow regions. In at least some embodiments, the non-conducting core is a flex circuit substrate and the conductors are conductive traces formed on the flex circuit substrate. In at least some embodiments, the conductors are cut from a conductive tube.

Yet another embodiment is an electrical stimulation system that includes any of the electrical stimulation leads described above, a control module configured and arranged to electrically couple to the electrical stimulation lead, the control module including a housing, and an electronic subassembly disposed in the housing; and a connector for receiving the lead, the connector having a proximal end, a distal end, and a longitudinal length, the connector including a connector housing defining a port at the distal end of the connector, the port configured and arranged for receiving the proximal end of the lead body, and connector contacts disposed in the connector housing, the connector contacts configured and arranged to couple to at least one of the terminals disposed on the proximal end of the lead body.

A further embodiment is a method for constructing an electrical stimulation lead. The method includes segmenting a conductive tube into a plurality of longitudinally extending conductors with each conductor separated from each adjacent one of the conductors by a non-conductive gap; arranging the conductors around a non-conductive core; electrically coupling the conductors to a plurality of electrodes; and electrically coupling the conductors to a plurality of terminals.

In at least some embodiments, segmenting the conductive tube includes laser cutting the conductive tube. In at least some embodiments, segmenting the conductive tube includes forming at least one of the conductors with of wide regions and narrow regions alternating with the wide regions, where each wide region has a maximum width and each narrow region has a minimum width, where the maximum width of each wide region is at least three times the minimum width of each narrow region. In at least some embodiments, the maximum width of each wide region is at least five times the minimum width of each narrow region.

In at least some embodiments, segmenting the conductive tube includes segmenting the conductive tube so that the plurality of conductors are arranged in a spiral, helical, or twisted arrangement.

Yet another embodiment is a method for constructing an electrical stimulation lead. The method includes providing a non-conductive flex circuit substrate with a plurality of conductive traces disposed along the flex circuit substrate with each conductive trace separated from each adjacent one of the conductive traces by a non-conducting gap; electrically coupling the conductive traces to a plurality of electrodes; and electrically coupling the conductive traces to a plurality of terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads or lead extensions that include elements for reducing tissue heating or other deleterious effects due to radio frequency (RF) irradiation, as well as methods of making and using the leads, lead extensions, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
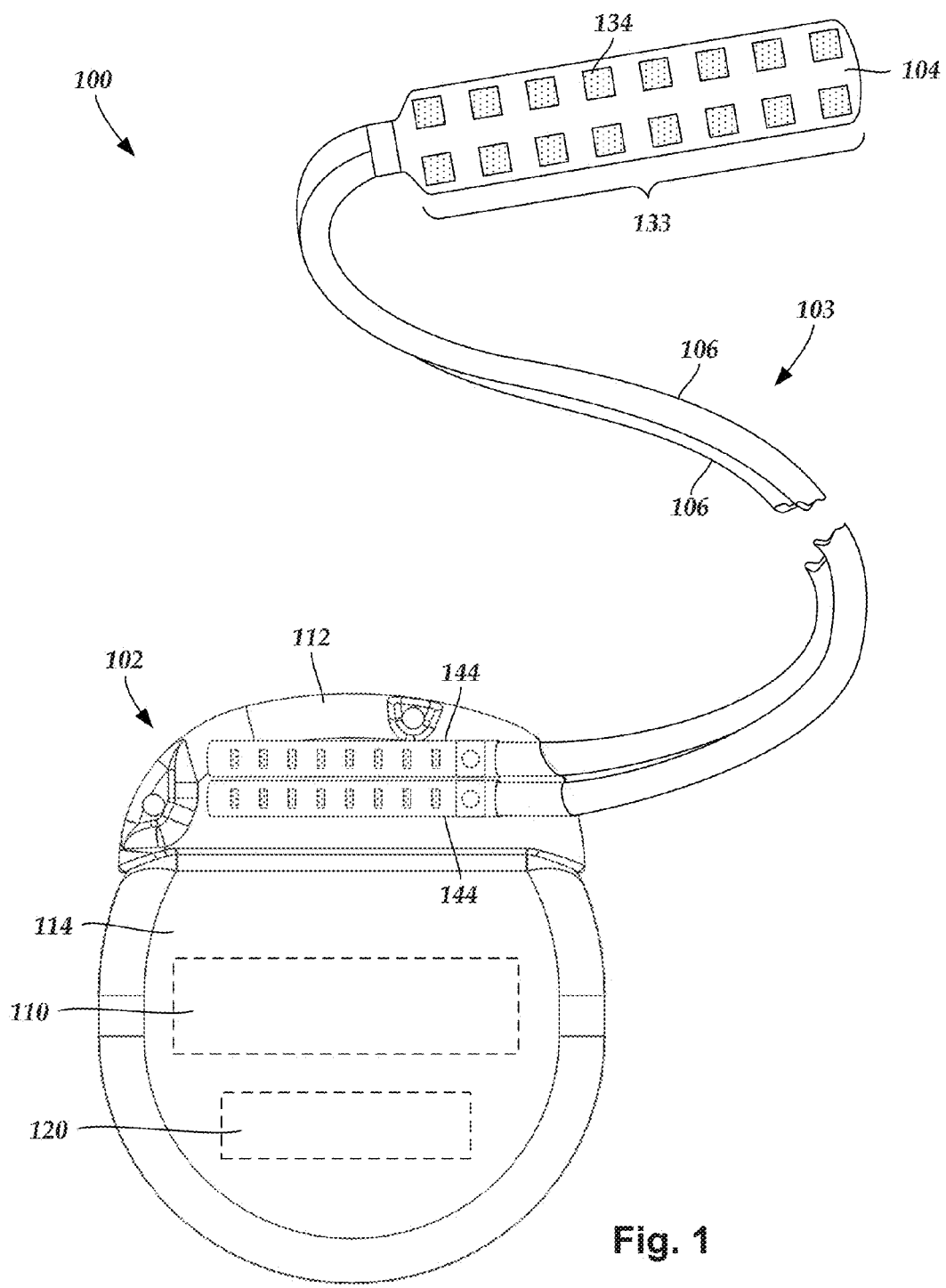
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
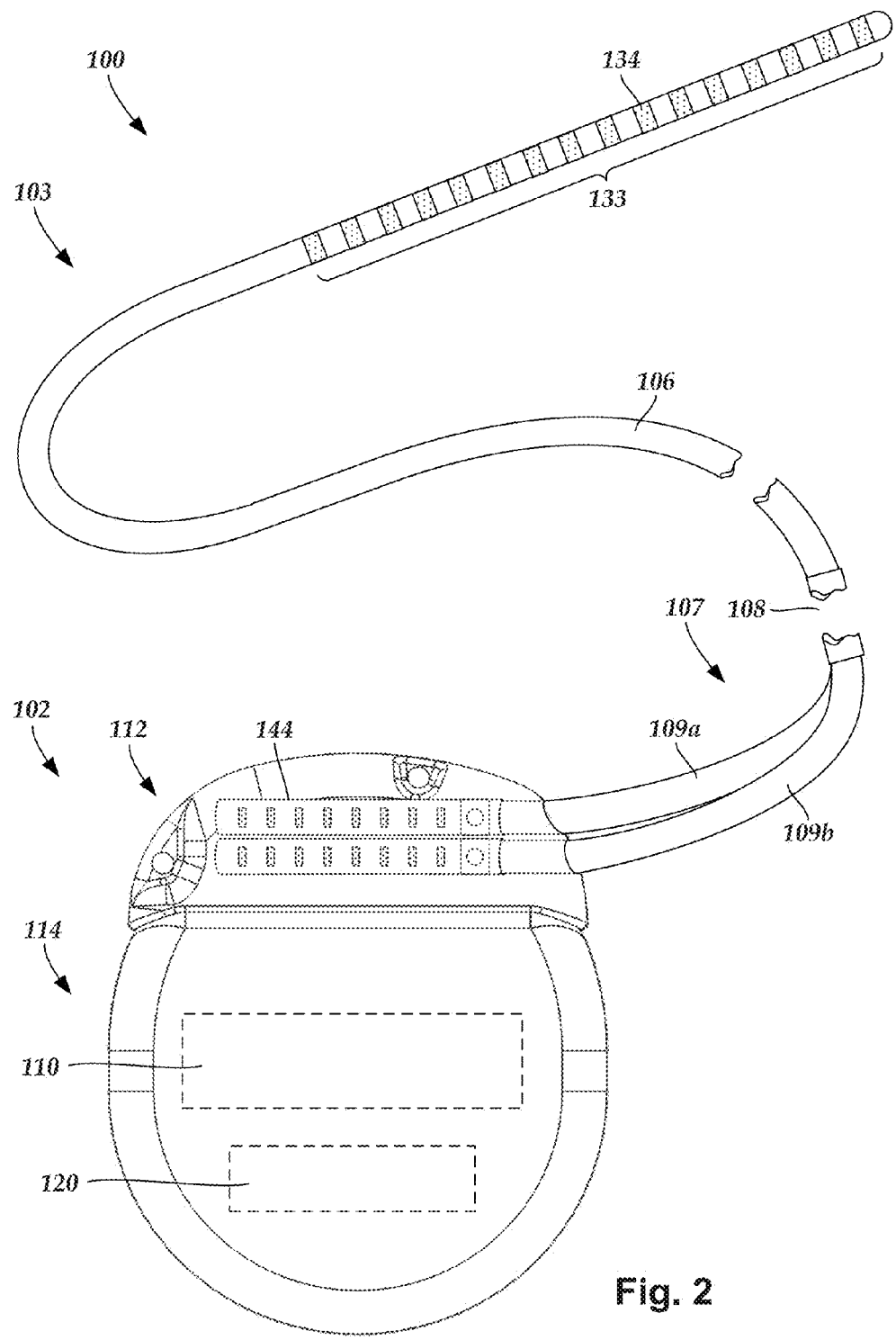
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 107 and 108A configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
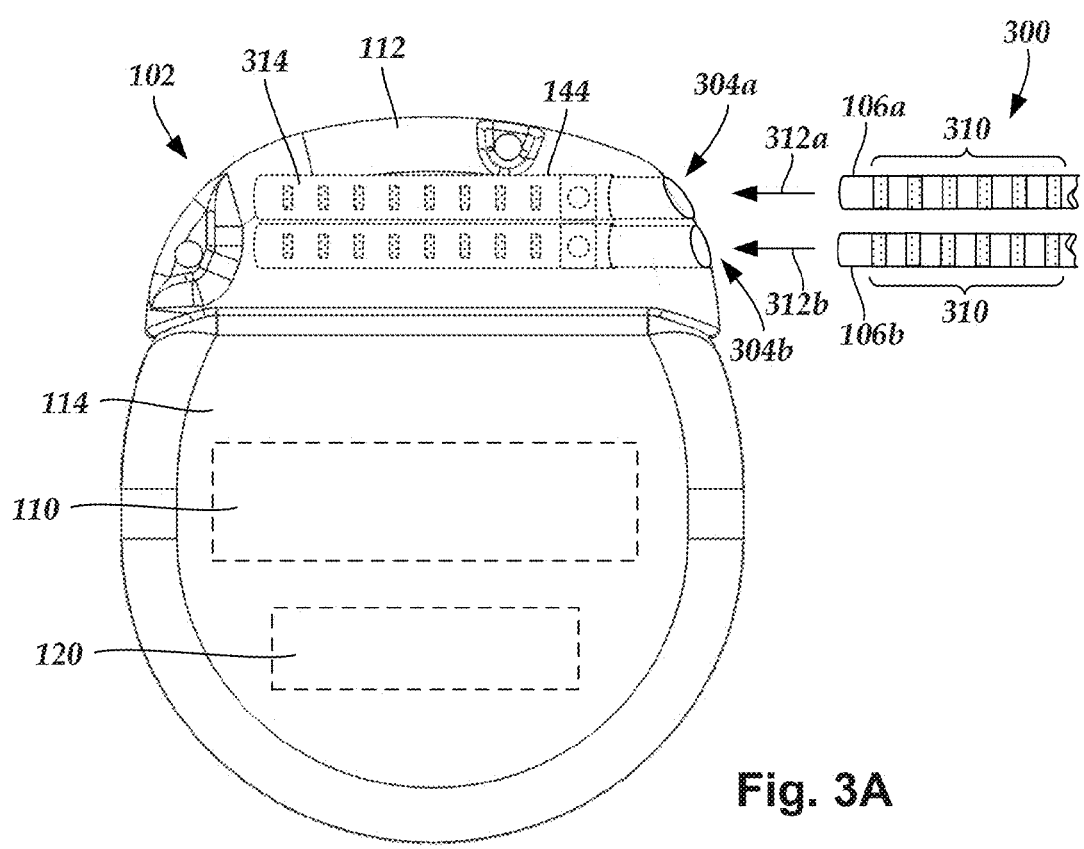
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
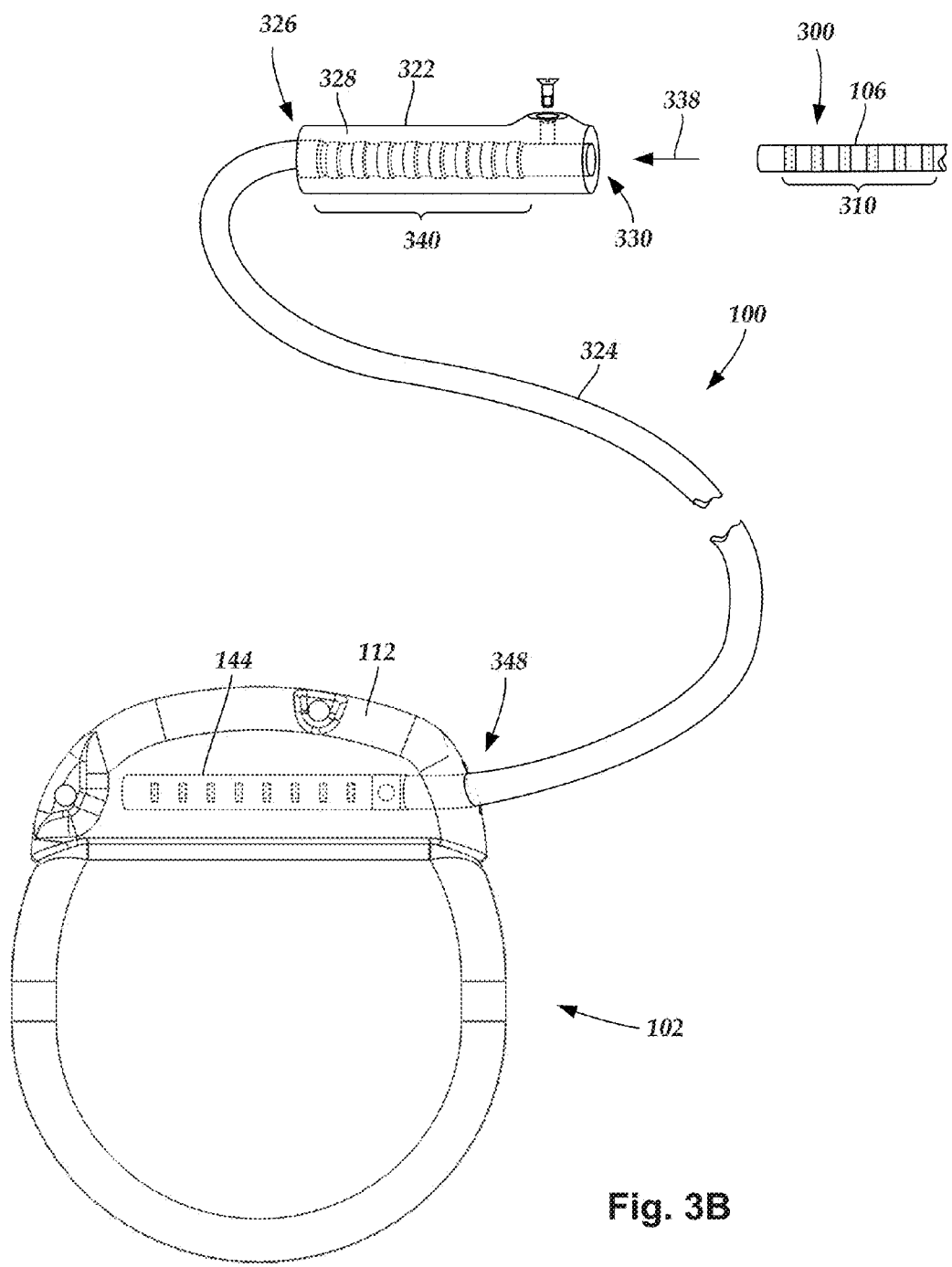
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Conventional electrical stimulation systems may be potentially unsafe for use when exposed to RF irradiation, such as during a magnetic resonance imaging ("MRI") procedure. A common cause of the electrical interaction between the electrical stimulation system and RF irradiation is common-mode coupling of the applied electromagnetic field. The interaction can be modeled as a series of distributed sources along the elongated conductive structures of the electrical stimulation system, such as leads, or conductors within leads. Common-mode induced RF currents may reach amplitudes of greater than one ampere in MRI environments. Such currents can cause heating and potentially disruptive voltages within electronic circuits.

Figure 4:
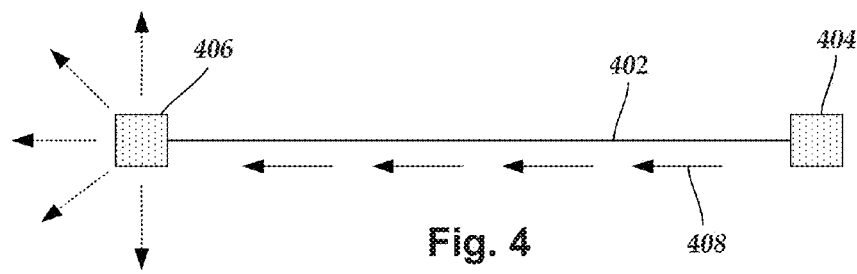
FIG. 4 is a schematic side view of one embodiment of a common-mode current propagation along an exemplary conductor of a lead, according to the invention.

FIG. 4 is a schematic diagram of one embodiment of a conductor 402 suitable for use in a lead (or lead extension). The conductor 402 extends between a terminal 404 and an electrode 406 (or a connector contact). When the conductor 402 is exposed to RF irradiation, such as when an implanted conductor 402 is in a patient undergoing an MRI procedure, a distributed electrical source (e.g., current, voltage), represented in FIG. 4 as arrows 408, can be formed and distributed along the conductor 402 by the coupling of incident electromagnetic fields within the conductor 402.

The electrical fields can become concentrated at the ends of the conductor 402, such as the terminal 404 and the electrode 406 (or connector contact), causing one or more undesired effects. Some of the undesired effects may include, for example, excessive heating that may potentially cause tissue damage, induced currents (potentially causing heating, undesired electrical stimulation, or device malfunction), undesired or unexpected operation of electronic components, or premature failure of electronic components.

To reduce these undesired effects to the electrical stimulation system and surrounding tissue, one or more properties can be selected along a length of the lead (or lead extension) to reduce the amount of current induced in the lead or to reduce the resulting power generated in the lead. As one example, the impedance of the lead can be decreased. Because the induced power is at least roughly proportional to impedance, decreasing the impedance can decrease the power induced in the lead.

Figure 5:
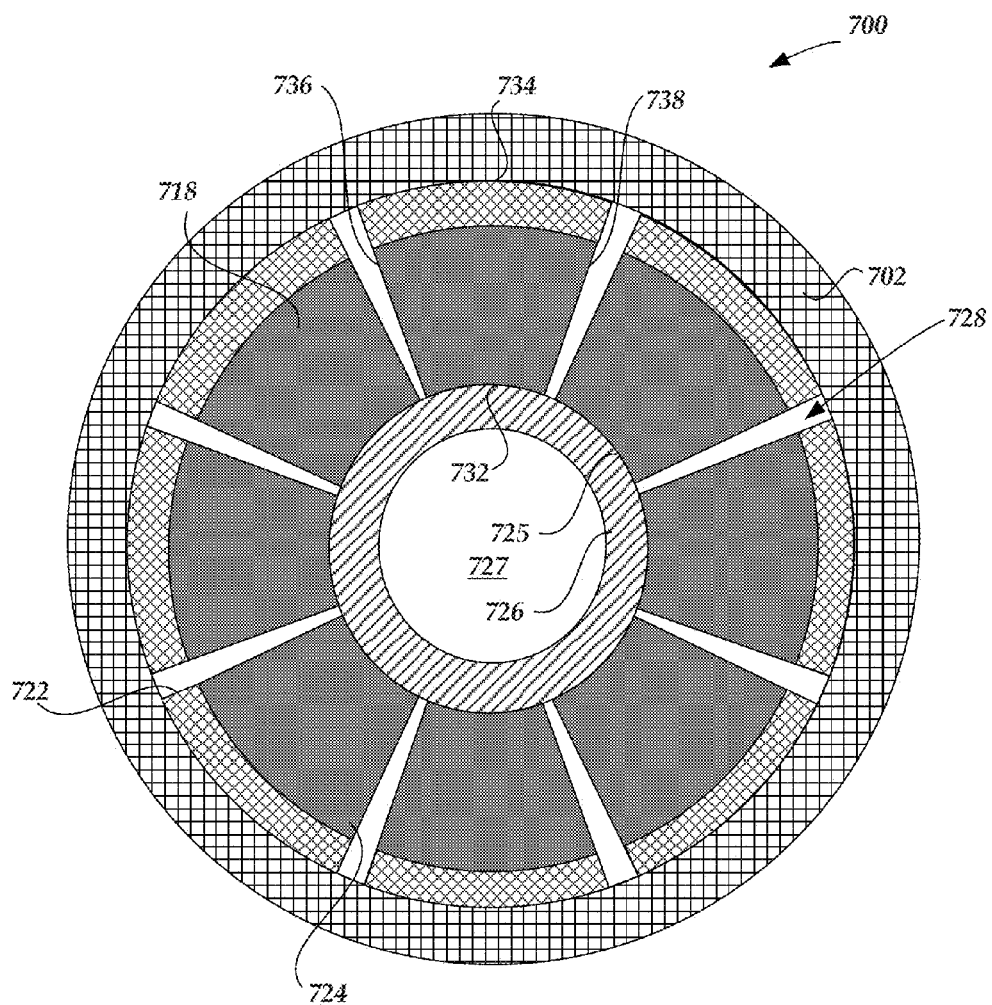
FIG. 5 is a schematic transverse cross-sectional view of one embodiment of a lead having conductors with an inner conductor portion and an outer conductor portion, according to the invention.

FIG. 5 is a transverse cross-sectional view of one embodiment of a lead 700. The plane of the transverse cross-section is substantially orthogonal to the longitudinal axis of lead 700, which extends into and out of the page. As discussed below, lead 700 provides an enhanced total capacitance (when compared to conventional leads which typically use wires) to lower the impedance of lead 700. Such a lowering of the impedance results in reduced RF heating arising from the lead 700.

Lead 700 includes multiple conductors extending or otherwise running along the longitudinal length of lead 700. In the embodiment shown in FIG. 5, lead 700 includes eight conductors 718. Other embodiments of lead 700 may include more or fewer than eight conductors. Accordingly, the longitudinal axis of each of the conductors 718 is substantially parallel with the longitudinal axis of lead 700. Any of the conductors discussed herein, and with respect to any of the disclosed embodiments, may include silver, MP35N alloy, gold, platinum, or any other conducting material as the conducting medium.

Each of the conductors is separated from each of the other conductors by a non-conductive gap so that there is no direct conduction path that enables a flow of direct current (DC) between the two conductors. These conductors may be capacitively coupled such that an AC signal may be transmitted or shunted between the two conductors.

The conductors are arranged around a core 726 that runs along the longitudinal length of lead 700. Core 726 includes a longitudinal axis that is substantially parallel with the longitudinal axis of lead 700. Core 726 is a non-conducting core and can be, for example, a mandrel. In at least some embodiments, the core 726 can include one or more lumens 727. FIG. 5 illustrates one central lumen 727 which may be, for example, a stylet lumen.

In addition, the lead 700 also includes a lead jacket 702 disposed around the conductors 718 and core 726. Lead jacket 702 is a non-conducting jacket, or constructed from any non-conducting material such as, but not limited to, polyurethane, fluorinated ethylene-propylene (FEP), or other polymer materials.

As shown in FIG. 5, the transverse cross-sectional shape of core 726 may be circular. However, in other embodiments, core 726 is not so constrained and may include a transverse cross-sectional shape of any regular or non-regular shape including, but not limited to oval, triangular, rectangular, hexagonal, and like shapes. The transverse cross-sectional shape of core 726 may be constant or variable along the length of lead 700. Core 726 includes an outer longitudinal surface 725.

The conductors 718 are arranged around core 726. In at least some embodiments, a portion of each of the conductors 718 is disposed against the outer longitudinal surface 725 of core 726. The conductors 718 are spaced around core 726 such that a non-conducting gap 728 is disposed between each adjacent pair of conductors. Each pair of conductors 718 is capacitively coupled and can be modeled as a capacitor. The mutual capacitance between a specific pair of conductors need not be equal to the mutual capacitance between another pair of conductors.

In the embodiment shown in FIG. 5, each of the conductors 718 has a transverse cross-section that is wedge-shaped or at least partially wedge-shaped. Each conductor 718 has an inner radial edge 732 and an outer radial edge 734, as well as two azimuthal edges 736, 738. Note, unless indicated otherwise, the terms "radial" and "azimuthal" are applied because the edges (and the corresponding longitudinal conductor surfaces) are characterized by a substantially constant radial or azimuthal coordinate in a polar coordinate system within the transverse cross-sectional plane. The origin of the polar coordinate system is located on the longitudinal axis of lead 700.

It should be understood that each of the plurality of conductors may include any other suitable transverse cross-sectional shape, such as, for example, an elliptical, triangular, rectangular, hexagonal, or any other regular or non-regular shape. In some embodiments, the transverse cross-sectional shape is uniform or otherwise constant with respect to the length of the lead 700. In other embodiments, the transverse cross-sectional shape is non-uniform or variable with respect to position along the longitudinal axis of the lead.

In at least some embodiments, the azimuthal position or orientation of the conductors may be constant along the length of the lead 700. In other embodiments, the azimuthal position may vary with the longitudinal position for at least one of the conductors. For instance, the plurality of conductors may form a twist, a partial twist, a spiral, a helix, or some other orientation that includes a variable azimuthal position, as a function of the longitudinal position (see, for example, FIG. 8A).

Each conductor may include a transverse cross-sectional that is the same or similar to the other conductors. In other embodiments, at least one of the conductors may include a transverse cross-sectional shape that is dissimilar to that of at least one other conductor.

In at least some embodiments, the inner edge 732 and the outer edge 734 are concentric edges or arcs (with respect to the longitudinal axis of lead 700). In at least some embodiments, the azimuthal edges 736, 738 are each a portion of a radial ray. The azimuthal surfaces, corresponding to the azimuthal edges 736, 738 illustrated in FIG. 5, of the conductors may be planar surfaces.

In at least some embodiments, the inner radial surfaces, corresponding to the inner edge 732, of the conductors 718 are disposed near or on the outer surface 725 of core 726. Likewise, the outer radial surfaces, corresponding to the outer edge 734, of the conductors are disposed near or on an inner surface of lead jacket 702. However, in other embodiments, another material, or medium is disposed intermediate the conductor radial surfaces and at least one of the core 726 or the lead jacket 702.

As shown in FIG. 5, in at least some embodiments the conductor inner radial surfaces are associated with a first radial distance from the longitudinal axis of the core 726 or lead 700. Likewise, the conductor outer radial surfaces are associated with a second radial distance from the longitudinal axis of the core 726 or lead 700. The second radial distance is greater than the first radial distance. In at least some embodiments, the conductor inner and outer radial surfaces are concentric with the core outer surface. The conductor inner radial surfaces include a radius of curvature that is substantially equivalent to the first radial distance. Similarly, the conductor outer radial surfaces include a radius of curvature that is substantially equivalent to the second radial distance. Thus, the outer radius of curvature is greater than the inner radius of curvature.

In the illustrated embodiment, the gap 728 between adjacent conductors 718 can vary in width. For instance, the gap 728 in FIG. 5 is a wedge-shaped gap and a width of the inner portion of gap 728 is less than a width of the outer portion of gap 728. In other embodiments, the width of the gap 728 can be constant.

The capacitance between any pair of conductors can be modified by any one of the following: the distance between the conductors, the surface area of the conductors, the shape of the conductors, the curvature of the conductors, and the like or any combination thereof. The capacitance can also depend on the permittivity or the polarizability (electric susceptibility) of any medium between pairs of opposing outer surfaces of the conductors. In the illustrated embodiment, the wedge-shape conductors is selected to produce a larger surface area and smaller distance between the conductors than could be achieved with cylindrical wires. Increasing the capacitance of the lead can decrease the total power within the lead as capacitance is roughly inversely proportional to impedance and power is roughly proportional to impedance.

The conductors 718 can also be constructed to present a material with higher electrical resistivity or higher resistance to the incident RF field. Typically, an external electromagnetic field will diminish as the field extends further into a material, such as the conductors 718. A skin depth, $\delta$, can be defined as the distance from a conductor's outer surface where the external electromagnetic field has dropped by a factor of $e^{-1}$ (or some other defined factor) from that at the outer surface. Generally, the skin depth decreases with increasing frequency. For at least some embodiments, to first order, $$\delta = \sqrt{\frac{2\rho}{\omega \mu_r \mu_0}},$$

where $\rho$ is the electrical resistivity of the material, $\omega$ is the angular frequency of the current, $\mu_r$ is the relative magnetic permeability of the material, and $\mu_0$ is the permeability of free space. In at least some embodiments, the skin depth can be determined or estimated using this formula. In other embodiments, a more accurate formula can be used to determine or estimate skin depth or other approximations can be employed to estimate skin depth. In yet other embodiments, the skin depth can be determined or estimated based upon experimental observations.

In many commercial embodiments, the conductors of leads are formed of materials with low electrical resistivity, such as MP35N alloy (a nickel-cobalt-chromium-molybdenum alloy), platinum, or platinum/iridium alloy. To take advantage of this skin effect, one or more of the conductors 718 can be formed with an inner conductor portion 724 and outer conductor portion 722 which are made of two different materials. The outer conductor portion 722 has a radial thickness of at least the skin depth at a selected RF frequency, such as a selected MM frequency (for example, a frequency in the range of 60 to 200 MHz, such as 64 MHz, 83 MHz, or 128 MHz). In at least some embodiments, the outer conductor portion 722 is formed of a material that has an electrical resistivity or resistance that is higher (for example, at least two, three, four, six, eight, or ten times higher) than an electrical resistivity or resistance, respectively, of the material used to form the inner conductor portion 724. For example, the inner conductor portion 724 can be formed of MP35N alloy, platinum, or platinum-iridium alloy and the outer conductor portion 722 can be formed of gold or silver.

Because the electromagnetic field will primarily only penetrate into the outer conductor portion 722 and because the outer conductor portion has a higher electrical resistivity or resistance than the inner conductor portion 724, the induced current in the conductor 718 will be less than if the conductor 718 were made entirely of the material used in the inner conductor portion 724. In contrast, the electrical stimulation signals from the control module will primarily travel along the lower resistance inner conductor portion 724. In some sense, the outer conductor portion 722 "shields" the inner conductor portion 724 from the RF field.

In at least some embodiments, the outer conductor portion 722 has a radial thickness of at least 10 µm, 20 µm, 25 µm, 40 µm, 50 µm, or 100 µm. In at least some embodiments, the outer conductor portion 722 has a radial thickness in a range of 10 to 400 µm or a range of 25 to 255 µm. In at least some embodiments, the inner conductor portion 724 has a radial thickness of at least 30 µm, 50 µm, 60 µm, 75 µm, or 100 µm. In at least some embodiments, the inner conductor portion 724 has a radial thickness in a range of 30 to 600 µm or a range of 50 to 500 µm.

Lead 700 may be constructed from any process. In at least some embodiments, a mandrel is used for the core 726. Each of the conductors 718 is constructed in the appropriate geometry (for instance, the desired transverse cross-sectional shape). The individual conductors are arranged on the central mandrel 726. The lead jacket 702 is added over the top of all the conductors 718. In at least some embodiments, the conductors 718 can be adhesively coupled, laminated, embedded, or molded onto the core 726.

The lead jacket 702 can be added via any suitable process, including but not limited to crimping, reflowing, heat shrinking, dip coating, adhesively coupling, laminating, and the like. The alignment of the conductors 718 gives rise to the capacitance between conductor pairs. The lead electrodes and terminals can be welded or otherwise coupled to the appropriate conductor and the lead arrays may be assembled. In at least some embodiments, the lead jacket 702 can fill or partially fill the gaps 728 between the conductors 718.

In at least one embodiment, the mandrel includes radial fins or blades to form the gaps, such as gap 728 between the adjacent azimuthal surfaces of adjacent conductor pairs. The radial fins form a plurality of wedge-shaped trenches or grooves that are configured and arranged to receive the plurality of conductors, including the inner and outer conductors. The core and/or radial fins may include a dielectric material to enhance the mutual capacitance between each of the pairs of conductors. In at least one embodiment, core 726 includes a lumen (such a lumen 840 of FIG. 6A) or other aperture to receive a stylet or other instrumentation, including but not limited to, a catheter or endoscope.

Figure 6A:
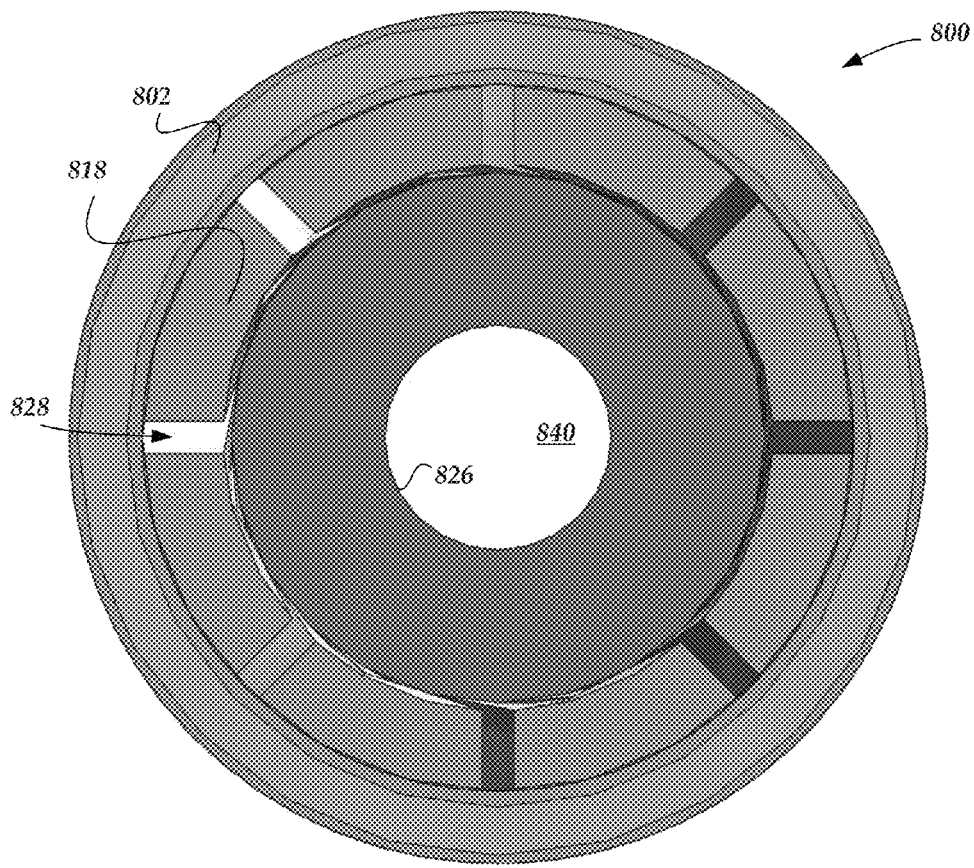
FIG. 6A is a schematic transverse cross-sectional view of another embodiment of a lead, according to the invention.

FIG. 6A is a transverse cross-sectional view of another embodiment of a lead 800 that includes eight conductors 818. Each of the conductors is separated from adjacent conductors by a non-conducting gap 826. In at least some embodiments, the conductors 818 can be conducting traces.

The lead 800 also includes a non-conductive core 826 which can be, for example, a mandrel or a flex circuit substrate. A non-conducting lead jacket 802 is positioned over the conductors 818.

Similar to the discussion of FIG. 5, higher capacitance between conductors can reduce the power induced in the lead by an external electromagnetic field and so the shape and arrangement of the conductors can be chosen to increase capacitance. Also similar to lead 700 of FIG. 5, lead 800 includes eight conductors but it should be understood that other embodiments are not so constrained and may include more or fewer than eight conductors.

Figure 6B:
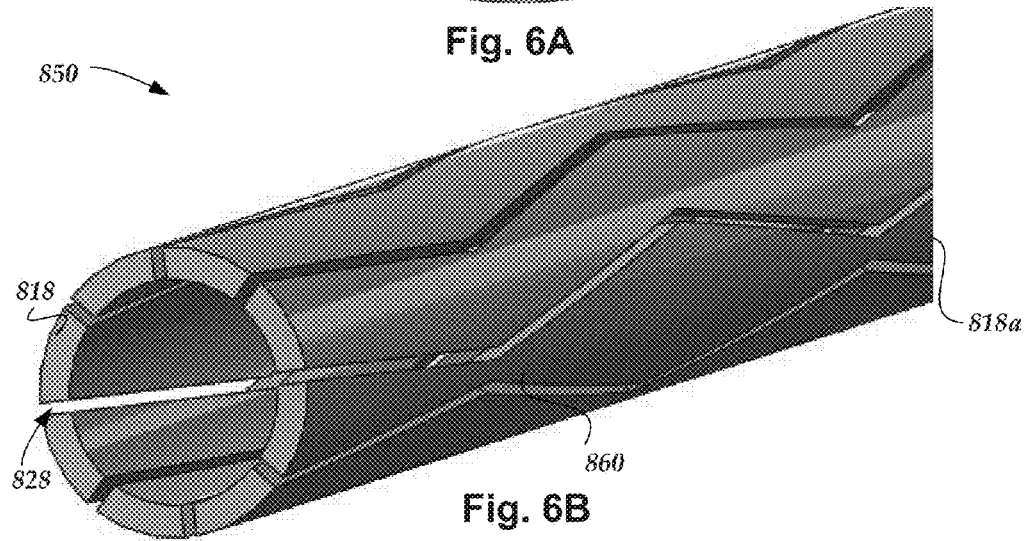
FIG. 6B is a schematic perspective view of a portion of one embodiment of a number of conductors formed from a tube that has been segmented, according to the invention.

In at least some embodiments, the conductors 818 of lead 800 can be formed by segmenting or otherwise cutting a conducting tube or the like. FIG. 6B shows a conducting tube 850 with gaps 828 cut between the conductors 818. The tube 850 can be formed by segmenting or cutting away portions of the tube to produce the conductors. The segmenting or cutting can be performed by any suitable method including laser cutting, blade cutting, and the like. The illustrated tube 850 has a circular cross section, however any other cross-sectional shape, such as rectangular, triangular, hexagon, octagonal or any other regular or irregular can also be used.

The tube 850 is preferably hollow to receive the core 826. The tube 850 can be disposed over the core 826 prior to or after forming the conductors. Core 826 may be a tubular member and include a lumen 840. Core 826 may be a mandrel of any transverse cross-sectional shape that is consistent with the transverse cross-sectional shape of the tube 850. In at least some embodiments, the conductors 818 are adhesively or otherwise coupled to the core 826.

In other embodiments, the conductors 818 can be formed as traces on the outer surface of the core 826. For example, the core 826 can be a non-conductive mandrel or flex circuit substrate that is initially covered with a metal coating. The conductors 818 can be formed by patterning the metal coating using any suitable technique including, but not limited to, photolithography, laser or other etching methods, or the like. In the case of the core 826 being a flex circuit substrate, the conductors 818 may be formed with the flex circuit substrate being planar and then the flex circuit substrate can be wrapped to form the cylindrical core 826 with conductors 818.

In at least some embodiments, the shape of at least some of the conductors 818 varies along the longitudinal length of lead 800. For instance, as shown in FIG. 6B, the conductors 818 can have a "zig-zag" shape. As such, the longitudinal edges of the inner and outer radial surfaces of the traces include portions with angled edges. In some embodiments, the conductors 818, such as conductor 816a, have regions with a larger width and regions with a smaller width. In at least some embodiments, such an arrangement with variable width can modify the distribution of power induced within the conductor and create multiple "power zones" distributed along the lead. Thus, instead of power flowing primarily to the electrodes or terminals, the induced power is distributed around the lead in a number of "power zones" and can be dissipated into tissue along the lead by, for example, capacitive coupling with the tissue or body fluids.

Figure 7:
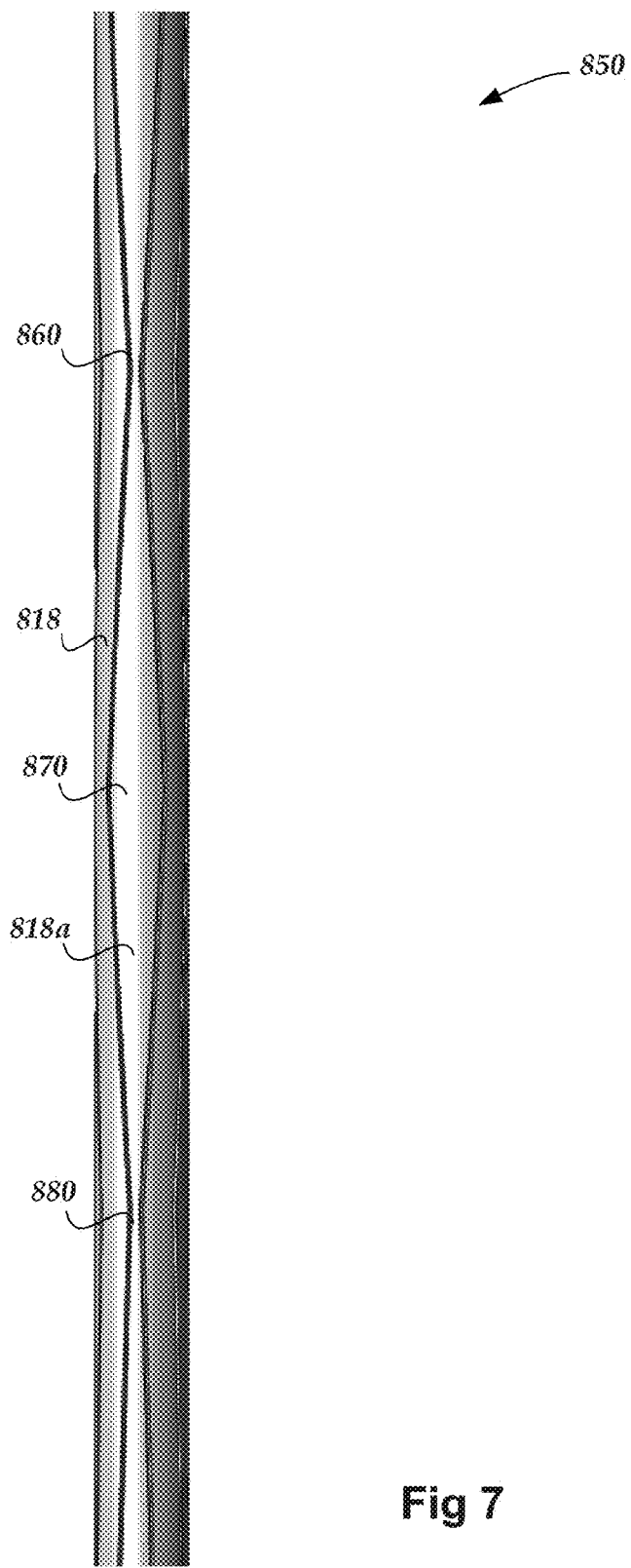
FIG. 7 is a schematic side view of a portion of another embodiment of conductors formed from a tube, according to the invention.

FIG. 7 illustrates another embodiment of a tube 850 with zig-zag-shaped conductors 818. One method for creating such power zones includes modulating the transverse cross-sectional area of one or more of the conducting traces. The conductor 816A has wide regions 870 and narrow regions 860, 880 where "wide" and "narrow" refer to the width of the conductor in the lateral or circumferential direction. In at least some embodiments, the maximum width of the wide regions is at least three, five, eight, ten, or twelve time the minimum width of the narrow regions.

Because the transverse cross-sectional area of the narrow regions 860, 880 is smaller than the transverse cross-sectional area of other portions of the conducting trace, such as wide region 870, the current density of the induced signals is increased at narrow regions 860, 880. The energy associated with these higher current densities may be dissipated from the lead by, for example, capacitively coupling to a patient's tissue.

Figure 8A:
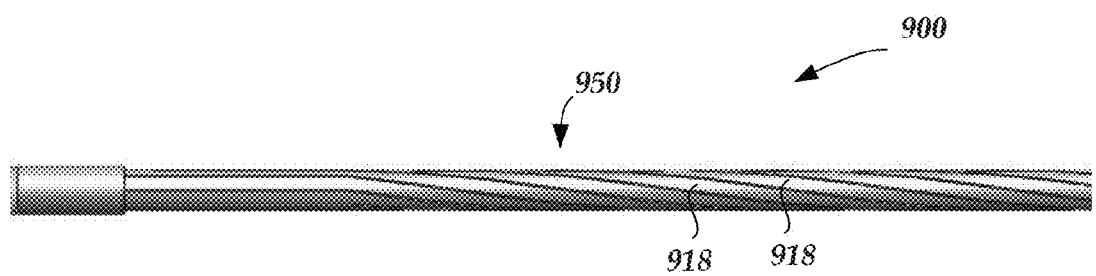
FIG. 8A is a schematic side view of a portion of another embodiment of a lead with spiraling conductors, according to the invention.

FIG. 8A illustrates a portion of another embodiment of a lead 900. Tube 950 defines conductors 918, where at least a portion of each of the conductors is helical, spiral, or twisting. Although not shown in FIG. 8A, tube 950 is concentrically placed over a non-conducting core.

Figure 8B:
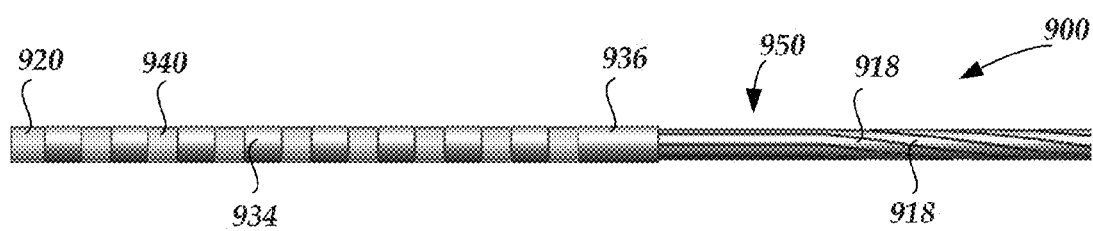
FIG. 8B is a schematic side view of the lead of FIG. 8A including an electrode array, according to the invention.

FIG. 8B shows a wider view of partially constructed lead 900. An array of electrodes, including at least electrodes 934 are formed on the lead body 920. An array of non-conducting spacers 940 are part of the lead body 920. The lead 900 also include a retention sleeve 936 that can be formed of metal and, optionally, also functions as an electrode.

It will be recognized that the conductors 818, 918 can also include the inner conductor portion and the outer conductor portion described with respect to conductors 718. It will also be recognized that the conductors 718 can be formed in a zig-zag, helical, twisted, or spiral arrangement as described with respect to conductors 818, 918 and may include the wide and narrow regions described with respect to conductor 818.

Figure 9:
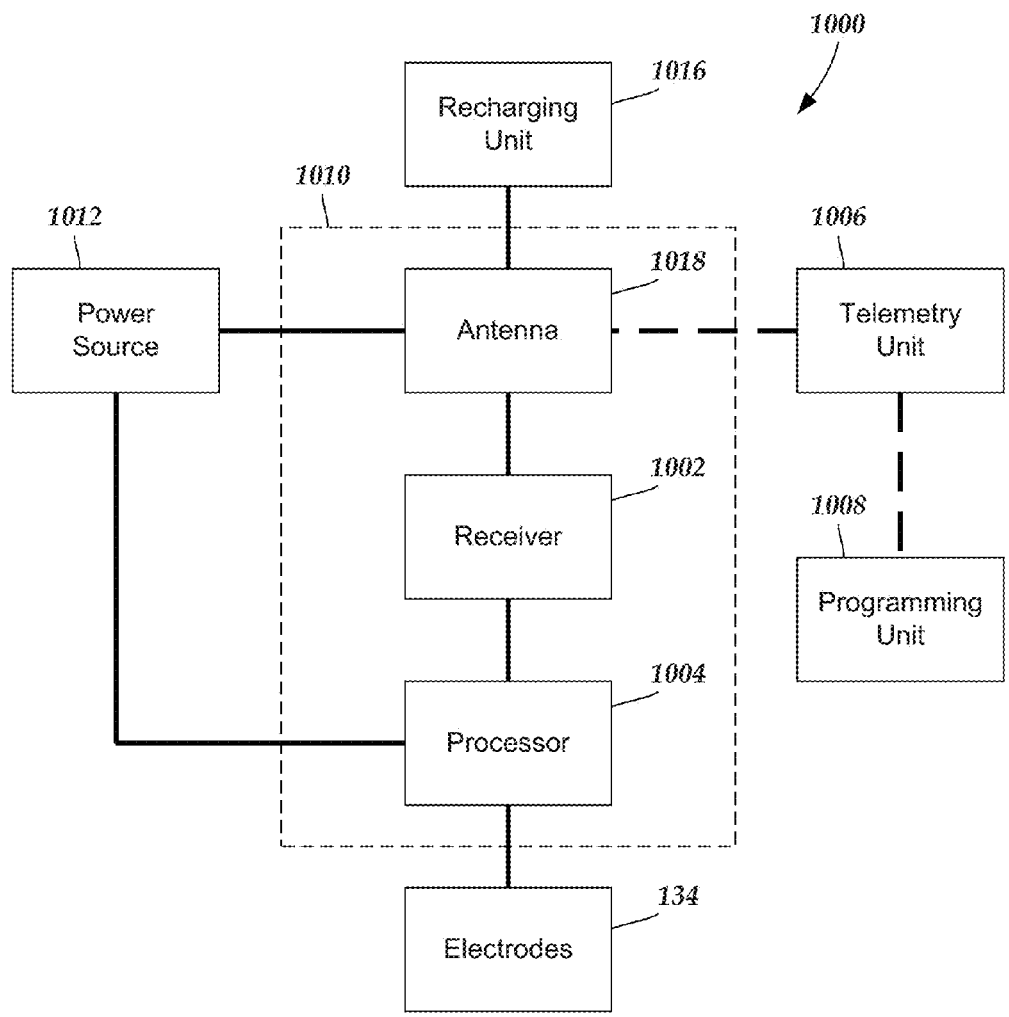
FIG. 9 is a schematic overview of one embodiment of components of a stimulation system, including an electronic subassembly disposed within a control module, according to the invention.

FIG. 9 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, a power source 1012, an antenna 1018, a receiver 1002, and a processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 selects which electrode(s) are cathodes and which electrode(s) are anodes. In some embodiments, the processor 1004 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by the programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and the receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include the antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
a lead body having a distal end, a proximal end, and a longitudinal length;
a plurality of electrodes disposed along the distal end of the lead body;
a plurality of terminals disposed along the proximal end of the lead body;
a non-conducting core extending along lead body; and
a plurality of conductors extending along the lead body to electrically couple the plurality of electrodes to the plurality of terminals, wherein the plurality of conductors comprises a first conductor and a second conductor arranged along the core with a non-conducting gap between the first and the second conductors,
wherein each of the first and the second conductors comprises an inner conductor portion with a first electrical resistivity and an outer conductor portion having a second electrical resistivity that is at least twice the first electrical resistivity, wherein the outer conductor portion is disposed exclusively radially outward from the inner conductor portion.

2. The electrical stimulation lead of claim 1, wherein a radial thickness of the outer conductor portion is at least equal to a skin depth of RF radiation at 64 MHz.

3. The electrical stimulation lead of claim 1, wherein each of the plurality of conductors is wedge-shaped.

4. The electrical stimulation lead of claim 3, wherein each of the conductors is separated from each adjacent one of the conductors by a wedge-shaped gap.

5. The electrical stimulation lead of claim 1, wherein the second electrical resistivity is at least five times the first electrical resistivity.

6. The electrical stimulation lead of claim 1, wherein the inner conductor portion is formed of MP35N alloy, platinum, or platinum/iridium alloy and the outer conductor portion is formed of gold or silver.

7. An electrical stimulation system, comprising:
the electrical stimulation lead of claim 1;
a control module configured and arranged to electrically couple to the electrical stimulation lead, the control module comprising
a housing, and
an electronic subassembly disposed in the housing; and
a connector for receiving the lead, the connector having a proximal end, a distal end, and a longitudinal length, the connector comprising
a connector housing defining a port at the distal end of the connector, the port configured and arranged for receiving the proximal end of the lead body, and
a plurality of connector contacts disposed in the connector housing, the connector contacts configured and arranged to couple to at least one of the plurality of terminals disposed on the proximal end of the lead body.

8. The electrical stimulation lead of claim 1, wherein both the inner conductor portion and the outer conductor portion extend along a longitudinal length of the first conductor.

9. The electrical stimulation lead of claim , the plurality of conductors comprises at least eight conductors.

10. The electrical stimulation lead of claim 1, wherein the non-conducting gap is wedge-shaped.

11. The electrical stimulation lead of claim 1, wherein the outer conductor portion has a radial thickness in a range of 10 to 400 µm.

12. The electrical stimulation lead of claim 11, wherein the inner conductor portion has a radial thickness in a range of 30 to 600 µm.

13. The electrical stimulation lead of claim 1, wherein a non-conducting gap is disposed between each adjacent pair of the conductors.

14. The electrical stimulation lead of claim 13, wherein each of the conductors is wedge-shaped and each of the non-conducting gaps is wedge-shaped.

15. The electrical stimulation lead of claim 14, wherein the non-conducting core comprises a mandrel with radial fins thrming the non-conducting gaps.

16. The electrical stimulation lead of claim 1, wherein the inner conductor portion is radially disposed exclusively between the outer conductor portion and the non-conducting core.

17. The electrical stimulation lead of claim 1, wherein the inner conductor portion and the outer conductor portion extend along an entire length of the first conductor.

18. The electrical stimulation lead of claim 1, wherein each of the conductors comprises the inner conductor portion and the outer conductor portion.

19. The electrical stimulation lead of claim 1, wherein each of the conductors comprises two opposing azimuthal edges with the azimuthal edges of each conductor facing one of the azimuthal edges of an adjacent one of the conductors to facilitate capacitive coupling between the conductors.

20. The electrical stimulation lead of claim 19, wherein the azimuthal edges are planar surfaces.

* * * * *